(12) United States Patent
Sankaran et al.

(10) Patent No.: US 11,707,325 B2
(45) Date of Patent: Jul. 25, 2023

(54) SYSTEM AND METHODS FOR ESTIMATION OF BLOOD FLOW USING RESPONSE SURFACE AND REDUCED ORDER MODELING

(71) Applicant: HeartFlow, Inc., Redwood City, CA (US)

(72) Inventors: Sethuraman Sankaran, Palo Alto, CA (US); David Lesage, Burlingame, CA (US); Charles Taylor, Atherton, CA (US); Nan Xiao, San Jose, CA (US); Hyun Jin Kim, San Mateo, CA (US); David Spain, Portland, OR (US); Michiel Schaap, Redwood City, CA (US)

(73) Assignee: HeartFlow, Inc., Mountain View, CA (US)

( * ) Notice: Subject to any disclaimer, the term of this patent is extended or adjusted under 35 U.S.C. 154(b) by 469 days.

(21) Appl. No.: 16/875,767

(22) Filed: May 15, 2020

(65) Prior Publication Data
US 2020/0360088 A1 Nov. 19, 2020

Related U.S. Application Data

(60) Provisional application No. 62/849,489, filed on May 17, 2019.

(51) Int. Cl.
*A61B 34/10* (2016.01)
*G16H 10/60* (2018.01)
(Continued)

(52) U.S. Cl.
CPC ............ *A61B 34/10* (2016.02); *G16H 10/60* (2018.01); *G16H 30/40* (2018.01); *G16H 50/50* (2018.01);
(Continued)

(58) Field of Classification Search
CPC ........ A61B 2034/105; A61B 2034/107; A61B 34/10; G16H 30/40; G16H 10/60; G16H 50/50
See application file for complete search history.

(56) References Cited

U.S. PATENT DOCUMENTS

2010/0017171 A1* 1/2010 Spilker .................. G16H 30/40
703/2
2015/0150530 A1* 6/2015 Taylor .................. A61B 5/0044
600/407

(Continued)

OTHER PUBLICATIONS

International Search Report and Written Opinion issued in International Application PCT/US2020/033239, dated Aug. 20, 2020.
(Continued)

*Primary Examiner* — Sing-Wai Wu
(74) *Attorney, Agent, or Firm* — Bookoff McAndrews, PLLC

(57) ABSTRACT

Systems and methods are disclosed for blood flow simulation. For example, a method may include performing a plurality of blood flow simulations using a first model of vascular blood flow, each of the plurality of blood flow simulations simulating blood flow in a vasculature of a patient or a geometry based on the vasculature of the patient; based on results of the plurality of blood flow simulations, generating a response surface mapping one or more first parameters of the first model to one or more second parameters of a reduced order model of vascular blood; determining values for the one or more parameters of the reduced order model mapped, by the response surface, from parameter values representing a modified state of the vasculature; and performing simulation using the reduced order model parameterized by the determined values, to determine a blood flow characteristic of the modified state of the vasculature.

18 Claims, 8 Drawing Sheets

(51) Int. Cl.
*G16H 30/40* (2018.01)
*G16H 50/50* (2018.01)
*A61B 5/026* (2006.01)

(52) U.S. Cl.
CPC ... *A61B 2034/105* (2016.02); *A61B 2034/107* (2016.02)

(56) References Cited

U.S. PATENT DOCUMENTS

| | | | |
|---|---|---|---|
| 2016/0125154 A1 | 5/2016 | Sankaran et al. | |
| 2016/0196384 A1* | 7/2016 | Mansi | G16H 30/20 600/408 |
| 2016/0303371 A1* | 10/2016 | Whiting | A61B 5/6831 |
| 2017/0018081 A1 | 1/2017 | Taylor et al. | |
| 2022/0107256 A1* | 4/2022 | Buoso | G16H 30/40 |

OTHER PUBLICATIONS

Gianluca Geraci et al., "Towards a Multi-fidelity Hemodynamic Model Pipeline for the Analysis of Cardiovascular Flow Under Uncertainty", SANDIA National Laboratories, SAND2017-8163C (2017) (46 pages).

Peter Benner et al., "A Survey of Projection-Based Model Reduction Methods for Parametric Dynamical Systems", SIAM Review., vol. 57, No. 4, Jan. 2015, (pp. 483-531).

Paris Perdikaris et al., "Model inversion via multi-fidelity Bayesian optimization: a new paradigm for parameter estimation in haemodynamics, and beyond", J. R. Soc. Interface 13: Nov. 7, 2015. http://dx.doi.org/10.1098/rsif.2015.1107 (2016) (15 pages).

* cited by examiner

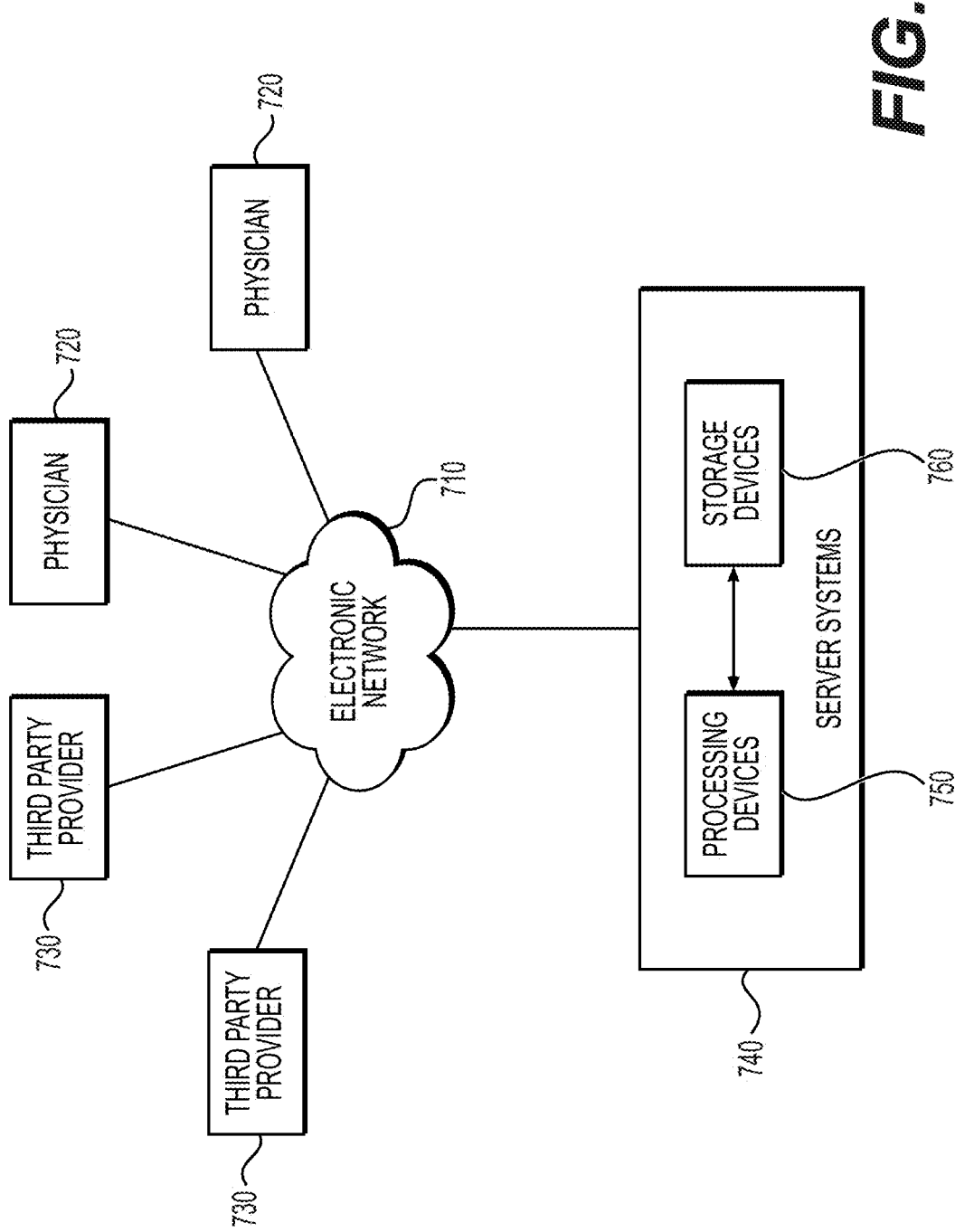

SYSTEM AND METHODS FOR ESTIMATION OF BLOOD FLOW USING RESPONSE SURFACE AND REDUCED ORDER MODELING

RELATED APPLICATION

This application claims priority to U.S. Provisional Application No. 62/849,489, filed May 17, 2019, the disclosure of which is hereby incorporated by reference in its entirety.

TECHNICAL FIELD

Various embodiments of the present disclosure relate generally to the prediction of the behavior of complex systems using a response surface and reduced order modeling, and, in particular, to efficient real-time estimation of blood flow using a response surface methodology and reduced order modeling.

BACKGROUND

Modeling and simulation of real-world physical phenomena may be performed to predict outcomes without invasive measurements. For example, many real-world physical phenomenma, such as the flow of blood in arteries, fluid flow in porous media, and large deformation processes, may be modeled using partial differential equations. Modeling and simulation may also be used to design and optimize systems to yield a desired outcome.

In clinical applications, blood flow characteristics may be relevant to assessing the health or disease of a patient. For example, hemodynamic indices may be used to assess the functional significance of lesions, blood perfusion levels, the transport of blood clots, the presence of aneurysms, and other health and disease characteristics. Hemodynamic indices may be measured invasively or assessed using blood flow simulation. While simulation techniques may be used to perform non-invasive assessments of the hemodynamics (based on available imaging data, for example), simulation techniques may also offer the potential benefit of predictive modeling of hemodynamics in response to various events (e.g., progression or regression of lesions) and predictive modeling of the outcome of planned procedures (e.g., surgical intervention). In order for predictive modeling to be realistic or clinically useful, it may be desirable or even necessary for modeling and simulation systems to be capable of computing results significantly faster than the average time needed to solve a high-fidelity model.

Fast computation of simulation results, such as real-time simulation, may assist clinicians and others in the planning of clinical procedures as well as the prediction of the impact of potential future events. In certain contexts, such predictions using simulation may have no invasive analogue. Thus, without the benefit of simulated results, a clinician may instead need to rely solely on available data and his or her knowledge, intuition and experience, when planning a procedure for a patient.

Therefore, there is a need for systems and methods for effectively performing real-time simulation using models of blood flow and other physical phenomena. Since accuracy and efficiency may be desirable factors, there is, in particular, a need for systems and methods that are capable of integrating accurate modeling with efficient algorithms to enable real-time estimation of simulation outcomes.

The present disclosure is, in various aspects, directed to addressing one or more of these above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, systems and methods are disclosed for blood flow simulation.

For example, a computer-implemented method may include: performing a plurality of blood flow simulations using a first model of vascular blood flow, each of the plurality of blood flow simulations simulating blood flow in a vasculature of a patient or a geometry based on the vasculature of the patient; based on results of the plurality of blood flow simulations, generating a response surface mapping one or more first parameters of the first model to one or more second parameters of a reduced order model of vascular blood flow having lower fidelity than that of the first model; determining values for the one or more parameters of the reduced order model mapped, by the response surface, from parameter values representing a modified state of the vasculature; and performing simulation of blood flow in the modified state of the vasculature using the reduced order model parameterized by the determined values for the one or more second parameters, to determine a blood flow characteristic of the modified state of the vasculature.

Furthermore, a system may include a memory storing instructions; and one or more processors configured to execute the instructions to perform a method. The method may include performing a plurality of blood flow simulations using a first model of vascular blood flow, each of the plurality of blood flow simulations simulating blood flow in a vasculature of a patient or a geometry based on the vasculature of the patient; based on results of the plurality of blood flow simulations, generating a response surface mapping one or more first parameters of the first model to one or more second parameters of a reduced order model of vascular blood flow having lower fidelity than that of the first model; determining values for the one or more parameters of the reduced order model mapped, by the response surface, from parameter values representing a modified state of the vasculature; and performing simulation of blood flow in the modified state of the vasculature using the reduced order model parameterized by the determined values for the one or more second parameters, to determine a blood flow characteristic of the modified state of the vasculature.

Furthermore, a non-transitory computer-readable medium storing instructions that, when executed by one or more processors, cause the one or more processors to perform a method. The method may include performing a plurality of blood flow simulations using a first model of vascular blood flow, each of the plurality of blood flow simulations simulating blood flow in a vasculature of a patient or a geometry based on the vasculature of the patient; based on results of the plurality of blood flow simulations, generating a response surface mapping one or more first parameters of the first model to one or more second parameters of a reduced order model of vascular blood flow having lower fidelity than that of the first model; determining values for the one or more parameters of the reduced order model mapped, by the response surface, from parameter values representing a modified state of the vasculature; and performing simulation of blood flow in the modified state of the vasculature using the reduced order model parameterized by the determined values for the one or more second parameters, to determine a blood flow characteristic of the modified state of the vasculature.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 7 illustrates an environment in which the a computer system for performing methods of the present disclosure may be implemented, according to one or more embodiments.

DETAILED DESCRIPTION OF EMBODIMENTS

Figure 1:
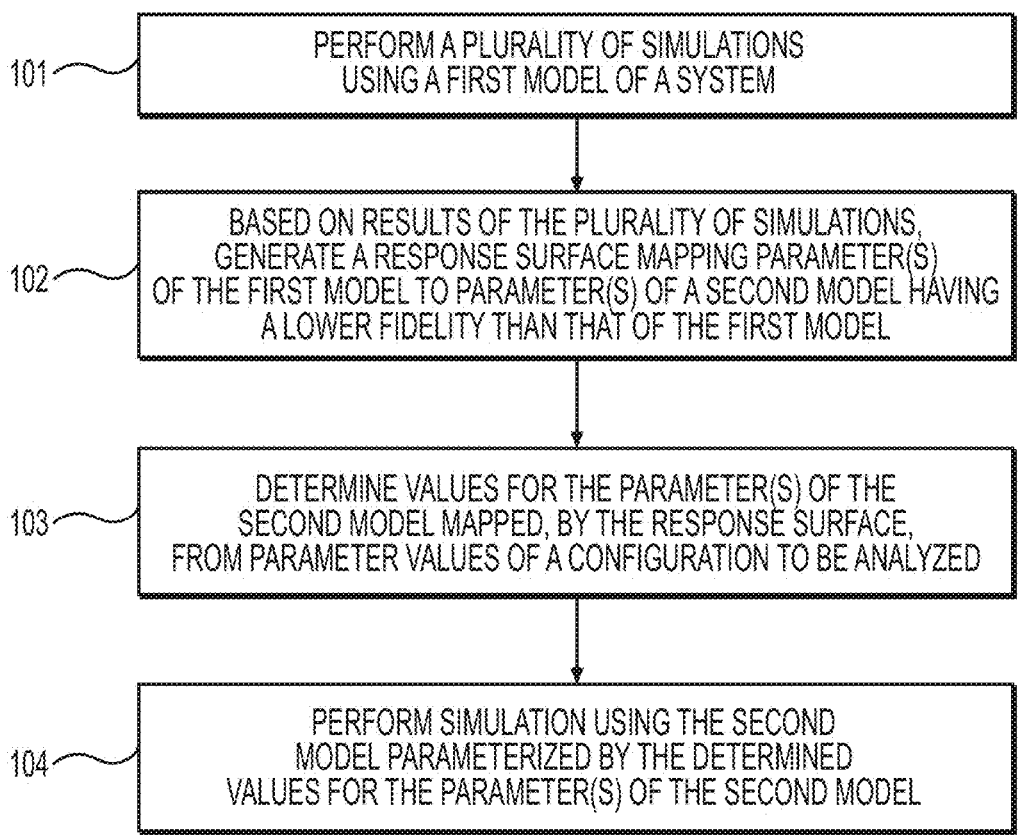
FIG. 1 depicts a flowchart of a method for estimating the behavior of a system using a response surface, according to one or more embodiments.

In various embodiments, systems and methods permit a reduced order model, derived from computational fluid dynamics (CFD), to be used to simulate complex systems in real-time with arbitrary accuracy as compared to the accuracy of a high-fidelity model. The high-fidelity model of a physical system may be computationally expensive. Therefore, the high-fidelity model may be unsuitable or impractical for real-time simulation. The reduced order model, on the other hand, may have a lower computational complexity than that of the high-fidelity model. Therefore, the reduced order model may be executed more quickly, so as to be more suitable for real-time simulation.

In order to use a reduced order model for real-time simulation while achieving an arbitrary accuracy, high-fidelity simulation using a high-fidelity model may be performed for a certain set of configurations. The results of the high-fidelity simulation may then be used to parameterize a reduced order model. As will be described in more detail below, the reduced order model may be parameterized using a response surface methodology according to the present disclosure. In this methodology, the results of the high-fidelity simulation performed for the aforementioned set of configurations may be used to generate a response surface, which may be a mapping of parameters of the high-fidelity model to the reduced order model. The response surface may then be used to parameterize the reduced order model.

Simulation using the parameterized reduced order model, which may be real-time simulation, may be capable of predicting results significantly faster than high-fidelity simulation using the high-fidelity model, while achieving an accuracy that is arbitrarily close to that of the high-fidelity simulation. The accuracy of the reduced order model, and hence the accuracy of the simulation using the reduced order model, may depend on the set of configurations that was used to generate the response surface. Therefore, the accuracy of the reduced order model and the reduced order modeling may be tuned by increasing or otherwise adjusting the configurations used to generate the response surface. For example, by refining the response surface, it is possible to ensure that the simulation using the reduced order model has an accuracy within some error margin. Additionally, since the high-fidelity simulation used to generate the response surface may be computationally expensive, the high-fidelity simulation may be performed offline, prior to performing real-time simulation using the reduced order model.

The methods of the present disclosure may enable fast prediction of the behavior of a complex system, such as changes in hemodynamics in response to changes in the state of a patient. Such changes in the state of a patient may be natural or planned (e.g., procedural). For example, in some embodiments, the methods of the present disclosure may be used to produce real-time updates of FFRCT in response to a change in vessel lumen geometry. This change in vessel lumen geometry may, for example, be a natural change, or a change that is expected to occur as a result of a candidate treatment.

In the following description, embodiments of the disclosure will be described in more detail, with reference to the accompanying drawings. The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. Relative terms, such as, "substantially" and "generally," are used to indicate a possible variation of ±10% of a stated or understood value.

In this disclosure, a reduced order model may also be referred to as a low-fidelity model or as a fast model. A reduced order model that is usable for real-time simulation may also be referred to as a real-time model. Furthermore, where context permits, reduced order models and high fidelity models may be general models that can be parameterized using different parameter values, such as different values corresponding to different configurations. In general, the term "parameter" may refer to a parameter of any type, including boundary conditions.

In the following description, a methodology for fast simulation of partial differential equations is provided. Initially, it is noted that, for purposes of building and parameterizing a reduced order model for fast prediction of behavior of complex systems, the following may be assumed: (i) there is a high-fidelity model that performs well for the system under consideration; (ii) information that is pertinent to the high-fidelity simulation (e.g., the original state of the patient geometry and the physiological state of the patient) is available; and (iii) it is possible to perform offline computations based on the information in (i) and (ii), wherein the offline computations may be not as fast as solving using a reduced order method. However, it is understood that the methods of the present disclosure may be practiced independently of the foregoing assumptions, and that assumptions are presented here for illustrative purposes only.

Let a general partial differential equation be of the form $$L(u;p)u(x^N)=0 \text{ in } \varphi \tag{1}$$

with boundary conditions $$b(u;p)=0 \text{ in } \varphi^B \tag{2}$$

where L is an operator (e.g., a differential, integral, functional or a combination thereof), u are unknowns, $x^N$ represents the problem dimensions, p represents given parameters, $\varphi$ is the problem domain, and $\varphi^B$ denotes the boundary of the domain. Expressions (1) and (2) may represent a system, and may serve as a high-fidelity model of the system.

A reduced order model of the partial differential equation may approximate the operator L using a simpler operator (e.g., ordinary differential equations), reduce the dimensionality, $x^N$, to an input space of the reduced order model, $x^n$, in which observation of the simulation results is of interest, and/or simplify the parameter set p to $\hat{p}$. The reduced order model may be expressed as follows:

$$\hat{L}(\hat{u};\hat{p})\hat{u}(x^n)=0 \text{ in } \hat{\varphi} \tag{3}$$

with the boundary conditions $$\hat{b}(\hat{u};\hat{p})=0 \text{ in } \widehat{\varphi^B} \tag{4}$$

A goal is to have $\hat{u}(x^n)$ be a reasonable approximation to $u(x^N)$, where $x^N$ may be a superset of $x^n$. A general approach is to perform simulations of the system, as originally formulated by expressions (1) and (2), for various boundary domains $\varphi^B$, boundary conditions $b(.)$, and parameter(s) such that a response surface may be used to generate an accurate approximation to the problem. Such simulations of the system may be referred to as high-fidelity simulations.

For purposes of generating the response surface, the domain $\varphi^B$ may have bounds as expressed below:

$$\varphi_L^B \leq \varphi^B \leq \varphi_U^B \tag{5}$$

The boundary conditions to which the system will be subject may have bounds as expressed below:

$$b_L(u) \leq b(u) \leq b_U(u) \forall u \tag{6}$$

Furthermore, the parameter space may have bounds as expressed below:

$$p_L(u) \leq p \leq p_U(u) \forall u \tag{7}$$

The original governing equation may be solved in a series of domains and boundary conditions $$(b_1(.),\varphi_1^B,p_1),(b_2(.),\varphi_2^B,p_2), \ldots (b_M(.),\varphi_M^B,p_M) \tag{8}$$

where M is the number of high-fidelity simulations performed. Each of the M terms expressed above may correspond to as a configuration for which high fidelity simulation is to be performed. That is, the M terms may represents M configuration.

In general, a "configuration" may refer to any modeling or simulation configuration, and may include any parameter (and its value). A configuration may be set of value(s) of such parameter(s). In the foregoing formulation, each of the M configurations may be represented as a set of values for the parameters of $b(.)$, $\varphi^B$, and/or p. The concept represented by a particular configuration may depend on the system that is being modeled. For example, if the system is blood flow through arteries of a patient, a configuration may represent a certain lumen geometry, a certain physiological state of the patient, or a combination thereof.

In general, any suitable method, such as a sampling method or a quadrature method, may be used in the selection of the M configurations. The results of the high-fidelity simulation for the M configurations may be expressed as:

$$u_1, u_2, \ldots u_M \tag{9}$$

The response surface, R, may be a mapping of the parameters of the high-fidelity model to the reduced order model:

$$\hat{p} \sim R(p,b(.),\varphi^B) \tag{10}$$

wherein $\hat{p}$ may capture the complexity of the original equations, enabling $\hat{L}$ to be a less complex operator than L. The response surface R may be obtained by any suitable method. If R uses point-fitting polynomials, such as Lagrange polynomials, then the reduced order model may be constructed such that $\hat{u}(x^n) = u(x^n)$ at the M configurations for which the high-fidelity simulations have been performed. That is, the reduced order model may be built to exactly match the output of the high-fidelity model for the M configurations. This approach allows a computer to solve the faster problem of $$\hat{L}\hat{u}(x^n)=0 \tag{11}$$

while ensuring that the results are identical at the M configurations. Approximations for the high-fidelity results at in-between configurations will generally be better for larger M, but so would the time needed for the offline computations.

In general, a high-fidelity model may include any number of mathematical relationships. Accordingly, a high-fidelity model may include multiple different mathematical relationships of the form given by expression (1) described above, and may include other mathematical relationships. Similarly, a reduced order may have multiple mathematical relationships, and may have multiple different mathematical relationships of the form given by expression (3) described above. In general, a high-fidelity simulation may utilize all information available about the system in question (e.g., the full spatial and temporal representation), and the high-fidelity model used for the simulation may include any number of full-order governing equations.

A response surface, such as response surface R, may be a mathematical relationship between a quantity or quantities of interest or parameters, and the underlying variables. A response surface may be a function (e.g., a fitted function) that maps input variable(s) (e.g., parameters of a high-fidelity model) to output variables (e.g., parameters of a reduced order model). The response surface may be built in a manner such that the response surface explores the parametric space using the reduced order model. Depending on the application or implementation, there may be multiple response surfaces. Different response surfaces may map between different respective parameters of the high-fidelity and reduced-order model.

FIG. 1 is a flowchart illustrating a method for estimating the behavior of a system using a response surface, according to one or more embodiments.

Step 101 may include performing a plurality of simulations using a first model of a system. The first model may be a high-fidelity model as described in this disclosure.

In some embodiments, the first model may be a high-fidelity model of vascular blood flow, and the simulations may be blood simulations that simulate blood flow in a vasculature of a patient or a vascular geometry based on the vasculature of the patient (e.g., a derived vasculature determined based on the vasculature of the patient). The term "vasculature of a patient" may refer to vasculature in any portion of the body of the patient. Examples of vasculature include, but are not limited to, coronary vasculature, peripheral vasculature, cerebral vasculature, renal vasculature, visceral vasculature, and hepatic vasculature such as portal veins. A derived vasculature may be, for example, a hypothetical vasculature having undergone a hypothetical modification to the vasculature of the patient.

While various embodiments pertaining to blood flow are described in this disclosure, the present disclosure is not limited to simulation of blood flow. In general, the formulations and techniques described in this disclosure, including those described for blood flow simulations, may be applied or generalized to other complex systems, including systems that may be characterized using computational fluid dynamics.

Step 102 may include generating, based on the simulation results obtained from step 101, a response surface mapping parameter(s) of the first model to parameter(s) of a second model having a lower fidelity than that of the first model. The second model may be a model having a lower fidelity than that of the first model, such as a reduced order model as described in this disclosure. Since the first model and the second model may respectively be the high-fidelity model and the reduced order model, as described above, the response surface may be a mapping of the parameter(s) of the high-fidelity model to the parameter(s) of the reduced order model. This mapping may be a function whose output is values for the parameter(s) of the reduced order model and whose input is values of the parameter(s) of the high-fidelity model.

Step 103 may include determining values for the parameter(s) of the second model mapped, by the response surface, from parameter values of a configuration to be analyzed. The parameter values of the configuration to be analyzed may be values for the aforementioned parameter(s) of the first model. In some embodiments, the first model may be a set of differential equations. Therefore, the parameter values of the configuration to be analyzed may be values of parameters (including boundary conditions) used in such differential equations. The values for the second parameter(s) may be determined by the response surface as a function of the parameter values of the configuration to be analyzed.

Figure 2A:
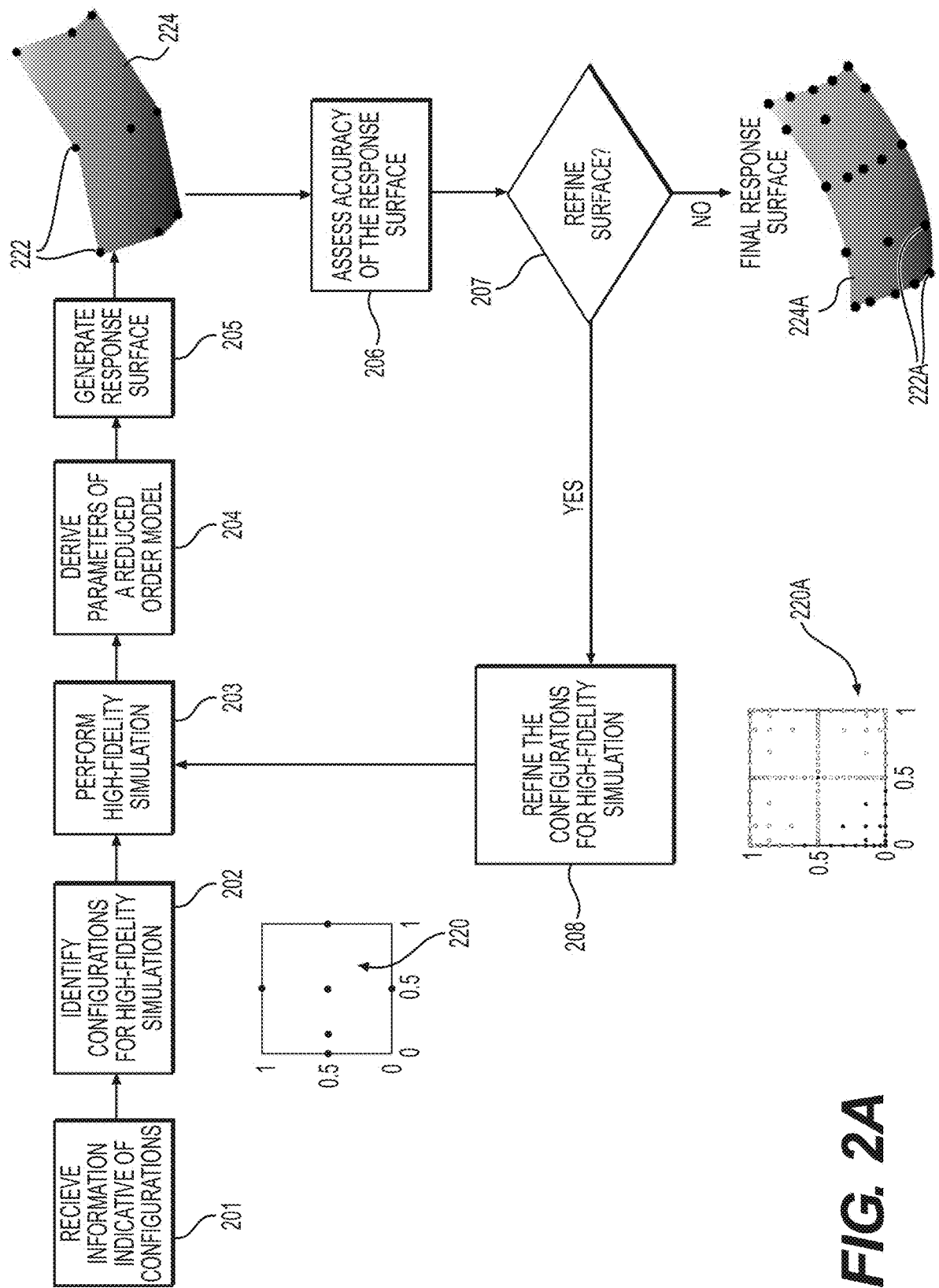
FIG. 2A illustrates a method of generating a response surface based on high-fidelity simulation, according to one or more embodiments.

Step 104 may include performing simulation using the second model parameterized by the determined values of the parameter(s) of the second model. For example, in the aforementioned embodiments pertaining to blood flow simulation, the parameter values for the configuration to be analyzed in step 103 may represent a modified state (e.g., a modified anatomical and/or physiological state) of the vasculature of the patient, in which case step 104 may determine a blood flow characteristic of the modified state of the vasculature. The simulation may be performed in real-time. The blood flow characteristic may be fractional flow reserve (FFR), flow magnitude, flow direction, FIG. 2A illustrates a method of generating a response surface based on high-fidelity simulation. The method of FIG. 2A illustrates an example implementation of the portion of the method of FIG. 1 corresponding to steps 101 and 102.

Step 201 may include receiving information indicative of configurations. Information indicative of a configuration may include, for example, one or more geometries (e.g., a geometry in which fluid flow is to be modeled or simulated), one or more boundary conditions, and/or any other parameters that may be part of a configuration. In some embodiments, the information indicative of configurations may be indicative of a range of possible configurations, in which case the information received in step 201 may be indicative of a range of values for the aforementioned parameters The information received in step 201, and may be manually input by a user or automatically determined by a process executed on the computer system.

Step 202 may include identifying configurations 220 for high fidelity simulation. Configurations 220 may be identified based on the information received in step 201. For example, if the information received in step 201 is indicative of a range of configurations, the configurations 220 identified in step 202 may be a sample of configurations within the range of configurations. Examples of sampling and quadrature methods are discussed below in connection with the method of FIG. 3. Configurations 220 may be identified automatically, or identified based on user input.

Step 203 may include performing high-fidelity simulation for the identified configurations for high-fidelity simulation. The configurations 220 identified in step 202 may be input into a high-fidelity model and high-fidelity simulation may be performed using the high-fidelity model parameterized in accordance with parameter values specified in the configurations 220.

Step 204 may include deriving parameters of a reduced order model. The parameters derived in step 204 may be derived based on configurations 220 identified in step 202 and the results of the high-fidelity simulation performed using high-fidelity model.

Step 205 may include generating a response surface 224. As described above, a response surface may be a mapping of the parameters of the high-fidelity model to the reduced order model. The results of simulation using the high-fidelity model and the parameters of the reduced order model may define a correspondence between values of the parameters of the high-fidelity model and values of the parameters of the reduced order model. Such correspondence may be represented as a set of points 222. The response surface 224 may then be generated based on the set of points 222. For example, the response surface 224 may be a surface fitted to points 222. The response surface may have an exact fit in that the surface 224 includes (intersects) all of points 222, as illustrated in FIG. 2A. However, such is not a requirement. Whether the surface 224 includes all of the points 222 may depend on the functional form of surface 224. As noted above, Lagrange polynomials may be used for an exact fit. In other fitting methods, it is possible for surface 224 to include only a portion of the points 223 or none of the points 223.

For example, the parameters of the reduced order model derived in step 204 may be a set of parameter values that, when used in simulation using the reduced order model, yields the same results as reduced order model computes to the same results of the high-fidelity simulations. For example, if N configurations for the high fidelity simulation specified respective parameter values of $(b_1(.), \varphi_1^B, p_1)$, $(b_2(.), \varphi_2^B, p_2), \ldots (b_N(.), \varphi_N^B, p_N)$ and such parameter values yield results of $u_1, u_2, \ldots u_N$ in high-fidelity simulation, then the parameter values derived in step 204 may be $\hat{p}_1, \hat{p}_2, \ldots, \hat{p}_N$, such that $\hat{p}_1, \hat{p}_2, \ldots, \hat{p}_N$, yield the same results $u_1, u_2, \ldots u_N$ in simulation using the reduced order model. Accordingly, the set of points 222 may be defined as $(\hat{p}_1, (b_1(.), \varphi_1^B, p_1)), (\hat{p}_2, (b_2(.), \varphi_2^B, p_2)), \ldots (\hat{p}_N, (b_N(.), \varphi_N^B, p_N))$, and response surface 224 may be generated as a surface fitted to these points. Such response surface may therefore provide the mapping relation as described above in connection with expression (10).

Step 206 may include assessing an accuracy of the response surface 224. Step 207 may determine, based on the accuracy assessed in step 206, whether response surface 224 is to be refined to have a higher accuracy.

The accuracy of a response surface may be defined by any suitable criteria. In some embodiments, accuracy may be a measure of accuracy in replicating results of the high-fidelity simulation. For example, the accuracy may be based on a closeness of results of reduced order modeling, when using the response surface 224 to parameterize the reduced order model for one or more testing configurations, to results of high-fidelity simulation for those one or more testing configurations. The one or more testing configurations may include one or more configurations different from the configurations represented by the points 222 based upon which the response surface 224 was generated.

Step 207 may resolve in "YES" if the accuracy of the response surface 224 assessed in step 206 is insufficient (e.g., not satisfying a predefined threshold condition), and may resolve in "NO" if the accuracy of the response surface 224 is assessed as being sufficient (e.g., satisfying a predefined threshold). In this context, accuracy may, for example, refer to accuracy of the reduced order model for arbitrarily defined configurations.

If step 207 resolves in "YES" (e.g., accuracy is insufficient), the method shown in FIG. 2A may proceed to step 208, which may include refining the configurations for high fidelity simulation. The process of refining the configurations may include adding new configurations for high fidelity simulation, removing existing configurations, and/or adjusting the values of existing configurations. For example, as shown in FIG. 2A, additional configurations may be added to the originally identified configurations 220 to improve accuracy of the response surface 224, so as to obtain a refined set of configurations 220A. Simulation using the high fidelity model (step 203) may be performed for any newly added configuration, such that the resulting response surface 224 is updated.

The decision of step 207 may implement a reiterated process in which the configurations for high fidelity simulation are refined (e.g., increased) in each subsequent iteration until the response surface 224 reaches a sufficient accuracy. Each configuration for which high-fidelity simulation is performed in step 203 may result in a corresponding point 222. Therefore, by adding additional configurations, the number of points 222 may be increased. Response surface 224 may then be fitted to the increased number of points 222 to as to potentially result in better accuracy.

When response surface 224 reaches a sufficient accuracy, step 207 may resolve in "NO," and the response surface 224 may then be accepted as final response surface 224A. As shown in FIG. 2, the points 222A of final response surface 224A, which may also be referred to as control points, may be more numerous than the points 222 of the initial response surface 224. The final response surface 224A also serves as an example of the aforementioned response surface R, in which case the set of configurations that is used to generate the final response surface 224A would serve as an example of aforementioned set of M configurations.

The method illustrated in FIG. 2A may be computationally expensive, depending on the time it takes to perform high-fidelity simulation for all configurations for which high-fidelity simulation is performed. Accordingly, the method may be performed offline. For example, the final response surface 224A may be generated in advance of real-time simulations using the reduced order model.

Figure 2B:
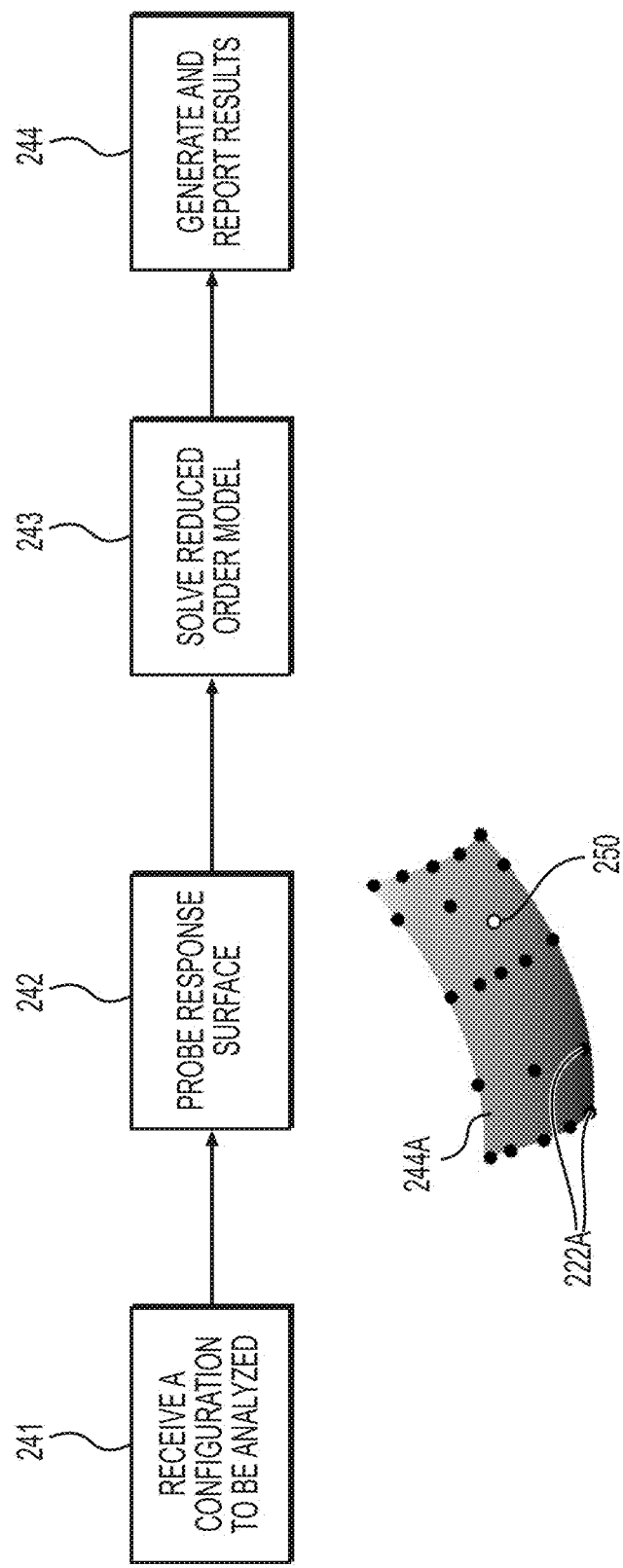
FIG. 2B illustrates a method for predicting simulation results in real-time based on the response surface generated using the method illustrated by FIG. 2A, according to one or more embodiments.

FIG. 2B illustrates a method for predicting simulation results in real-time based on the response surface 224A generated using the method of FIG. 2A. The method of FIG. 2B illustrates an example implementation of the portion of the method of FIG. 1 corresponding to steps 103 and 104.

Step 241 may including receiving a configuration to be analyzed. The configuration may be defined by any suitable method. For example, the configuration may represent the settings of a certain experiment to be performed via reduced order simulation. In this disclosure, the terms "configuration to be analyzed" and "configuration to be explored" are used interchangeably.

Step 242 may include probing the response surface. The probing process may determine a value of a parameter (e.g., a parameter in parameter set p) of the reduced order model for the configuration to be analyzed. The probing process is illustrated using point 250, which represents a value of a parameter for the reduced order model for the configuration to be analyzed. As shown, point 250 may be a point that is mapped from the configuration to be analyzed. For example, the configuration to be analyzed may have values of the parameters p, b, and $\varphi^B$ discussed above, and the response surface may determine the value of $\hat{p}$ as a function of those values of p, b, and $\varphi^B$. That is, point 250 may have a position on response surface 224A corresponding to the aforementioned values of $\hat{p}$, p, b, and $\varphi^B$ may have may represents a position having the determined value of $\hat{p}$. Since the positions on response surface 224A may be interpolated from the positions of points 224A, the position of point 250 may therefore be at an interpolated position.

Step 243 may include solving the reduced order model using the mapping given by the response surface 225. Step 204 may include solving expression (11) as described above. Steps 242 and 243 may be performed in real time as part of real-time simulation.

Step 244 may include generating and reporting the results of the simulation. For example, the results may be stored in an electronic storage device, or presented to a user (e.g., displayed on a display). Since the solving of the reduced order model may be a real-time process, the results of the reduced order model may also be presented in real-time.

Therefore, the prediction of the behavior of a complex system may include a first process of generating the response surface, as described in relation to FIG. 2A, and a second process of fast probing of the response surface to estimate results (e.g., hemodynamic indices) for a particular configuration, as described above in relation to FIG. 2B. As noted above, the first process of building the response surface may be performed offline and be computationally expensive, depending on the time it takes to perform high-fidelity simulations using a high-fidelity model. The computational expense of may depend on the acceptable error for the second process.

Figure 3:
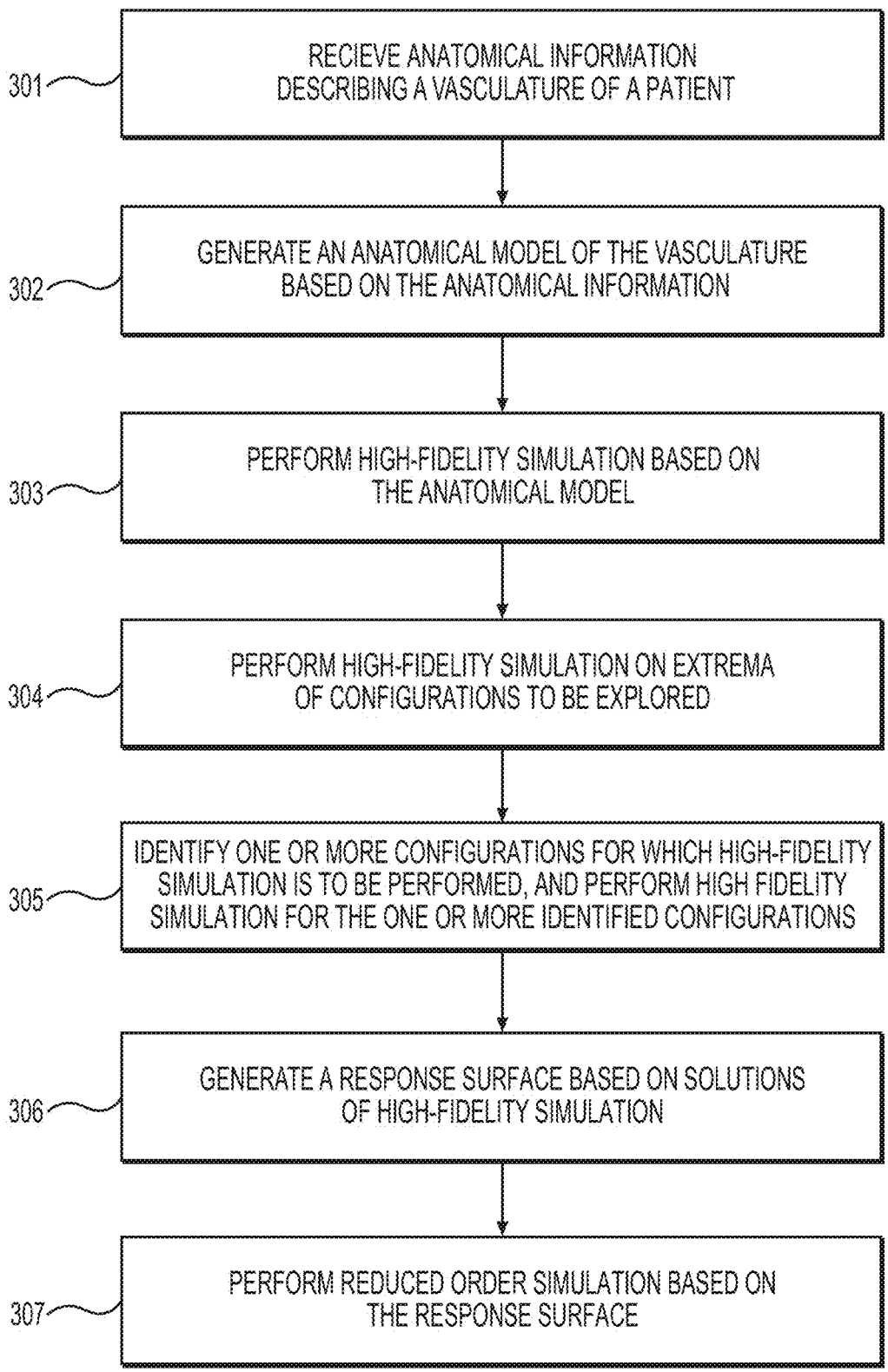
FIG. 3 is a flowchart illustrating a method for modeling the effect of changing lumen geometry and boundary conditions on blood flow simulation, according to one or more embodiments.
Figure 4:
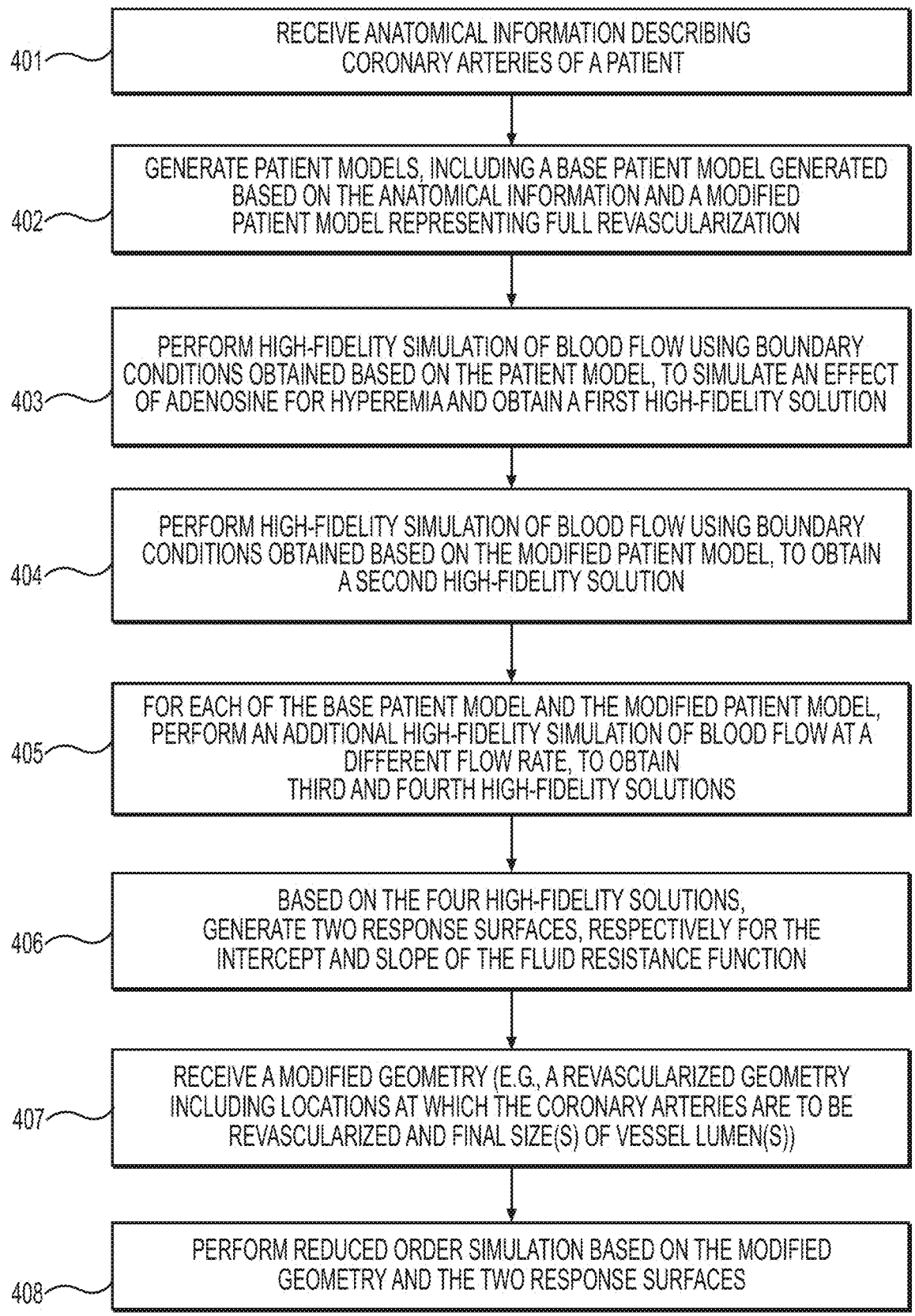
FIG. 4 is a flowchart illustrating a method for modeling the effect of revascularization of coronary arteries, according to one or more embodiments.

FIGS. 3 and 4 illustrate further examples in which the techniques described above are applied. FIG. 3 is a flowchart illustrating a method for modeling the effect of changing lumen geometry and boundary conditions on blood flow (e.g., coronary flow) simulation. The method may apply various techniques described above to perform real-time estimation of blood flow in arteries (e.g., coronary arteries) under a given new configuration. In this context, the given new configuration may be, for example, a lumen geometry and/or physiological state of a patient. The method of FIG. 3 may be performed by any suitable computer system.

Step 301 may include receiving anatomical information describing a vasculature of a patient. The described vasculature may include all arteries of the patient that are of interest. In some embodiments, the vasculature may be a coronary vasculature, in which case the anatomical information may describe the coronary arteries of the patient. As described above in connection with FIG. 1, examples of other types of vasculature include, but are not limited to, peripheral vasculature, cerebral vasculature, renal vasculature, visceral vasculature, and hepatic vasculature such as portal veins.

The anatomical information may be received from a memory (e.g., a hard drive or other electronic storage device) of the computer system performing step 301, or from another computer system (e.g., a computer system of a physician or third party provider) over a computer network.

In some embodiments, the anatomical information may include one or more images of the patient acquired using an imaging or scanning modality, and/or information extracted from (or otherwise obtained based on analysis of) such images of the patient. Examples of imaging or scanning modalities include computed tomography (CT) scans, magnetic resonance (MR) imaging, micro-computed tomography (μCT) scans, micro-magnetic resonance (μMR) imaging, dual energy computed tomography scans, ultrasound imaging, single photon emission computed tomography (SPECT) scans, and positron emission tomography (PET) scans. Such images of the patient may be received from a physician or third party provider over a computer network and/or stored in the memory of the computer system performing step 301. Since the images describe the patient's specific anatomical and physiological characteristics, any model that is derived from or constructed based on such images, or other patient-specific information, may be regarded as a patient-specific model. It is noted that use of the term "patient" is not intended to be limiting. A "patient" may generically be referred to as a "person."

Step 302 may include generating an anatomical model of the vasculature, based on the anatomical information received in step 301. The anatomical model may be of any suitable form and may model any suitable aspect of the vasculature. For example, the anatomical model may describe the patient-specific, three-dimensional geometry of the blood vessels of the vasculature as discerned from the anatomical information. In some embodiments, the anatomical model may indicate disease progression or regression, plaque rupture, thrombosis, and other characteristic of the represented vasculature(s). An anatomical model of a vasculature may also be referred to as a patient-specific anatomical model or a patient-specific vascular model. In some embodiments, the anatomical model may model the characteristics of the vasculature under one or more physiological states of the patient. In such embodiments, the characteristics of the anatomical model may reflect characteristic of the vasculature when the patient is in a certain physiological state (e.g., a resting state or an exercising state).

Examples of methods for generating anatomical models are described in, for example, US 2012/0041739 A1 ("US '739") to Taylor, which is hereby incorporated by reference in its entirety. It is noted that US '739 also provide examples of other aspects discussed in this disclosure, such as reduced order models and the calculation of fractional flow reserve (FFR).

Steps 301 and 302 may be performed by the same computer system that performs the remaining steps 304 to 307 described below. However, it is also possible for steps 301 and 302 to be performed by another computer system, in which case the anatomical model provided to the computer system that performs the remaining steps over a communication network. Any anatomical model received over a communication network may be stored in the memory of the computer system.

Step 303 may include performing high-fidelity simulation based on the anatomical model generated in step 302. The simulation may be a blood flow simulation that simulates the flow of blood in the arteries as modeled by the anatomical model. The high-fidelity simulation may involve detailed mathematical relationship(s) describing the system. Such mathematical relationships may include partial differential equation(s), such as the Navier-Stokes equations, in any suitable formulation. The high-fidelity simulation may be performed using any suitable technique(s), such as finite element analysis, finite difference methods, lattice Boltzmann methods, etc. The detailed mathematical relationship used in the high-fidelity simulation may constitute a high-fidelity model that is executed to perform the high-fidelity simulation.

For example, the detailed mathematical relationships may include Navier-Stokes equations with boundary conditions and/or other parameters derived from the anatomical model. The boundary conditions and/or other parameters may, for example, represent the geometry or other characteristics of the arteries as modeled by the anatomical model.

Step 304 may include performing high-fidelity simulation on extrema of configurations to be explored. Such simulations may be a blood flow simulation that simulates the flow of blood in a structure represented by the extrema of the configurations to be explored.

In this context, the configurations to be explored may be any configuration that is intended to be explored (e.g., simulated or otherwise studied) using the reduced order simulation described below. The extrema of the configurations to be explored may depend on the extrema of the parameter space and domain that is able to be explored using the reduced order model. Bounds may be imposed based on the limits of exploration. Such bounds may be application-specific. It is noted that the extrema of configurations to be explored, as described above, may be configurations for purposes of generating a response surface and may also be referred to as extrema configurations.

In some embodiments, one or more bounds may be imposed based on anatomical limits. For example, an upper bound on the anatomical model may be imposed based on a maximally allowable dilation for a patient-specific model. In this case, the patient-specific model may model the relieving of lumen narrowing at various locations, the effect of applying a higher level of nitrate, or a combination thereof. A maximally allowable dilation in such treatment situations may be represented as an upper bound on the anatomical model. In some embodiments, one or more bounds imposed based on anatomical limits may represent the addition or removal of vessels. For example, in the case of a bypass graft, an upper bound may be the maximum number of anastomoses based on available grafts.

Additionally or alternatively, one or more bounds may be imposed based on physiological limits. For example, to assess different physiological states of a patient, an upper bound and/or a lower bound may be assessed based on resting-state and exercise conditions or based on other extrema of the boundary conditions. For example, an upper (or lower) bound may represent a restating state of the patient, and an lower (or upper) bound may represent an exercising state of the patient.

Step 305 may include identifying one or more configurations for which high-fidelity simulation is to be performed, and performing high-fidelity simulation on the one or more identified configurations. It is noted that step 305 serves an example of steps 202 and 203 discussed above in connection with the method of FIG. 2A.

The larger the set of parameters and domains, the better the accuracy of the response surface and the accuracy of the real-time prediction. Any sampling or quadrature method may be used to identify the one or more configurations, including (but not restricted to): a Monte-Carlo sampling method, a Latin hypercube sampling method, a Gaussian quadrature method, a Sparse-grid quadrature method, an adaptive sparse-grid quadrature method, and combinations thereof. Monte-Carlo sampling may be appropriate in sampling a large-dimensional parameter space but may converge very slowly for problems with moderate-dimensional parameter space. Latin hypercube sampling may achieve separation of the parameter space and may converge better than Monte-Carlo for moderate-dimensional parameter space. In a Gaussian quadrature method, Gauss points may be used to generate the configurations and tensor-product interpolation may be used to scale the points to higher dimensions. A sparse-grid quadrature method may be the same as the Gaussian quadrature method for one dimension but may have a sparser grid to reduce the number of simulations. A adaptive sparse-grid quadrature method may be the same as the sparse-grid quadrature but may adapt to the function so that regions of shallow variations are explored less than regions of significant variations.

After identification of the one or more configurations on which high-fidelity simulation is to be performed, step 305 may further include performing high fidelity simulation on the one or more identified configurations.

Step 306 may include generating a response surface based on solutions of high-fidelity simulation. As described above, the response surface may be created based on high-fidelity solutions at a plurality of configurations (e.g., M configurations) using any functional form. In the context of FIG. 3, the M configurations referred to in the foregoing discussion may include any of the configurations identified in step 305, and may also include any configurations simulated in step 303 and/or step 304. Locally linear interpolation or Lagrange-polynomial interpolation may be performed to ensure that the solutions of the real-time simulation at the control points match the solution of the full simulation. In general, step 306 may utilize any of the techniques described above in connection with steps 204, 205, 206, and 208 of FIG. 2A.

In some embodiments, multiple response surfaces may be generated. For example, if the high-fidelity simulation involved multiple mathematical relationship (e.g., a mathematical relationship in the form of expression (1)) and/or the reduced order model includes multiple mathematical relationship (e.g., a mathematical relationship in the form of expression (3)), then multiple response surfaces may be generate to map between different combinations of high-fidelity and reduced order mathematical relationships. Furthermore, the response surface of step 306 may be revised by refining the configurations used to generate the response surface, as described above in connection with FIG. 1.

Step 307 may include performing reduced order simulation based on the response surface. The reduced order simulation may be informed by interpolated values estimated by the response surface. For example, as described above in connection with FIG. 2B, the response surface may be probed based on one or more configurations to be explored, to obtain the interpolated values. The one or more configurations to be explored may depend on the application of the method.

The reduced order simulation may be performed using a reduced order model, which may be constructed to exactly match the output of the high-fidelity model for the M configurations where high-fidelity simulations were performed. The reduced order simulation may be performed in real-time.

The method of FIG. 3 may include any one or more of the additional exemplary aspects described below, all of which are optional. These aspects may be implemented into one or more steps of the method described above, or implemented as additional steps of the method.

In some examples, the method of FIG. 3 may include quantifying confidence intervals. For example, the response surface created in step 306 may be probed to run many simulations, from which confidence interval estimates for the unknown fields may be calculated. For purposes of quantifying confidence intervals, the configurations to be explored may include any configuration suitable for quantifying the confidence intervals. For example, the configurations may be representative of configurations on which reduced order modeling is intended to be performed. The confidence interval estimates may be, for example, used to assist a clinician performing the reduced order simulation in understanding the accuracy of the reduced order model in performing similar types of simulations. Alternatively, the confidence interval estimates may be used to revise the response surface generated in step 306.

In some examples, the method of FIG. 3 may include modeling disease progression and/or regression. For example, the response surface generated in step 306 may also be probed to predict the impact of lesions that might progress or regress. In turn, these may be used for patient management and monitoring. The configurations to be explored may include any configurations suitable for modeling or simulating disease progression and/or regression.

In some examples, the method of FIG. 3 may include the modeling of different physiological conditions. For example, the response surface generated in step 306 may also be probed to model different physiological conditions (e.g., resting and exercise conditions) or the effect of pharmacological agents. The configurations to be explored may include any configurations suitable for modeling or simulating physical conditions.

While the method of FIG. 3 has been described for certain applications pertaining to blood flow, the techniques described for the method of FIG. 3 may be applied to other complex systems, including other fluid dynamics systems.

Figure 5:
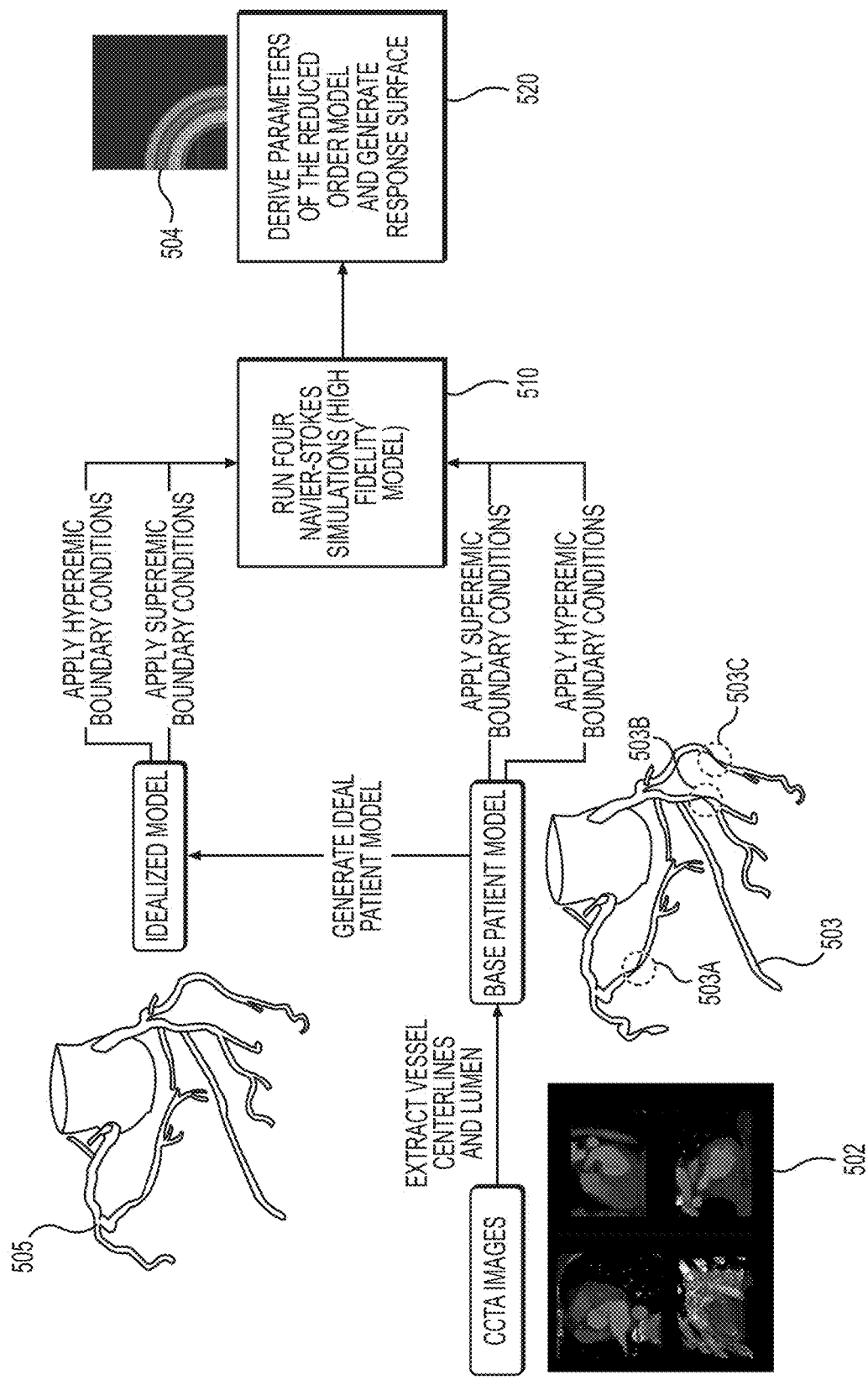
FIGS. 5-6 illustrates an exemplary implementation of the method of FIG. 4, according to one or more embodiments.
Figure 6:
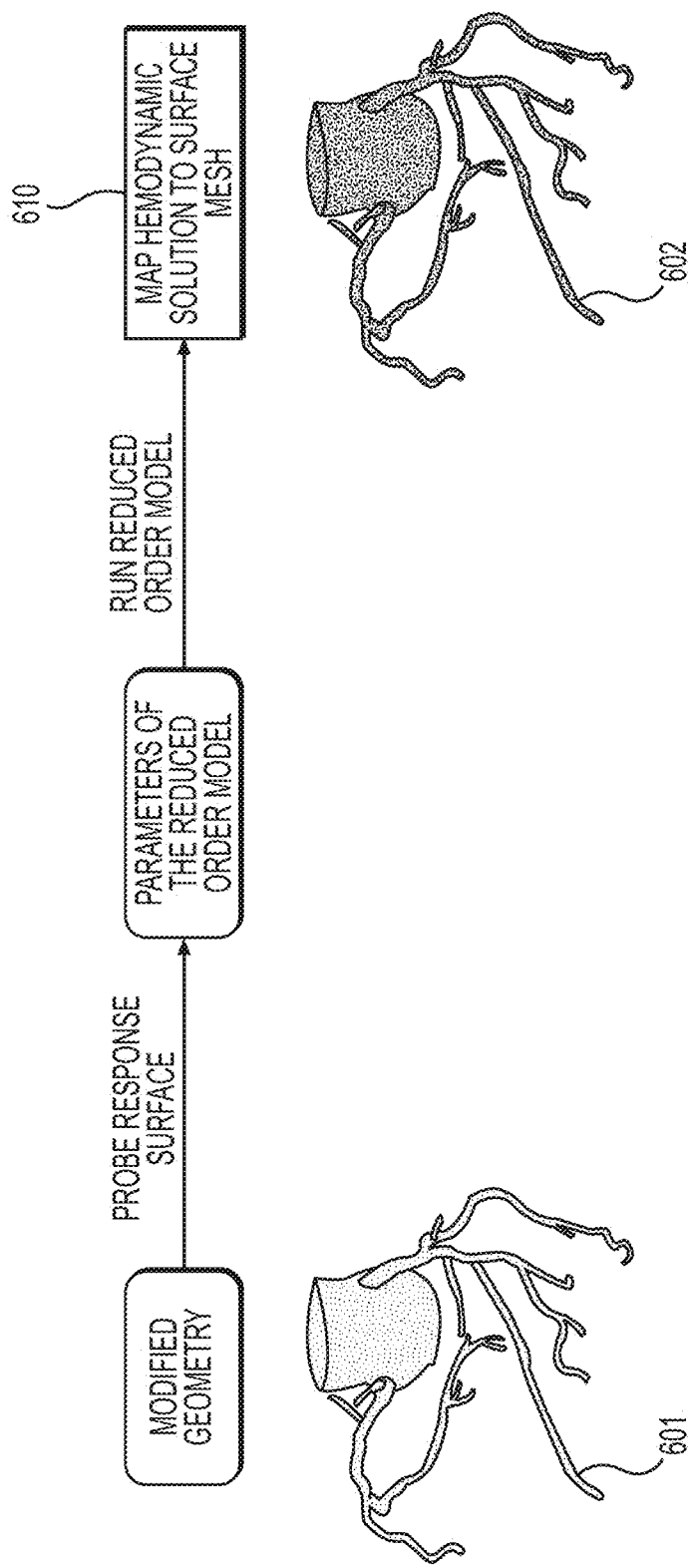

FIG. 4 is a flowchart illustrating a method for modeling the effect of revascularization of coronary arteries. The method may apply various techniques described above to perform real-time computational of the effect of revascularization of coronary arteries on blood flow. An exemplary implementations of the method of FIG. 4 is illustrated by FIGS. 5-6, also discussed below. The method of FIGS. 4-6 may be performed by any suitable computer system.

Step 401 may include receiving anatomical information describing coronary arteries of a patient. Step 401 may include any of the aspects of step 301 described above. In some embodiments, step 401 may include receiving anatomic information obtained from analysis of coronary CT scans. For example, as shown in FIG. 5, anatomical information describing anatomical characteristic of a patient, such as vessel centerlines and lumens, may be extracted from CCTA images 502 taken of the patient.

Step 402 may include generating patient models, which may include a base patient model and a modified patient model. The base patient model may be generated based on the anatomical information received in step 401. The modified patient model may be a modification of the base patient model. In some embodiments, the coronary arteries of the patient may have narrowed lumens, and the modified patient model may represent a full revascularization of the coronary arteries.

The base patient model may be an anatomical model that model actual anatomical characteristics (e.g., vessel centerlines and lumens) of the patient's coronary arteries, as described by the anatomical information. For example, as shown in FIG. 5, base patient model 503 may be generated based on vessel centerlines and lumens extracted from the CCTA images 502. In FIG. 5, base patient model 503 is illustrated as having a narrowed geometry at various locations 503A, 503B and 503C of the model. The narrowed geometry may model, for example, stenosis at corresponding locations of the patient's coronary arteries.

The modified patient model may be the base patient model having been modified to model a change in characteristics of the patient's coronary arteries. For example, the modified patient model may model a hypothetical condition of the patient's coronary arteries. Such condition may be, for example, an idealized condition corresponding to an extrema of configurations to be explored, in which case the modified patient model may be referred to as an idealized model. In FIG. 5, idealized model 504 is an example of a modified patient model that models the coronary arteries under a condition in which the entire anatomy represented by the base patient model is revascularized. For example, as shown in FIG. 5, the stenosis at locations 503A, 503B and 503C of the base patient model 503 are not indicated by the idealized model 504. In such embodiments, the modified patient model may be a revascularized anatomical model.

Step 403 may include performing high-fidelity simulation of blood flow using boundary conditions obtained based on the patient model, to simulate an effect of adenosine for hyperemia and obtain a first high-fidelity solution. In general, the boundary conditions in step 403 may be boundary conditions derived from characteristics of the patient, such as the patient's anatomy, myocardium, scaling laws for resting blood flow. Such boundary conditions may include boundary conditions be obtained based (e.g., derived from) the patient model. However, the present disclosure is not limited thereto, and it is also possible for some or all of the boundary conditions to be derived from other models or information.

The high-fidelity simulation of step 403 may be performed by constructing a computational model in the form of a high-fidelity model. The computational model may include mathematical relationships, such as Navier-Stokes equations and boundary conditions derived from the patient's anatomy, myocardium, scaling laws for resting blood flow. Such boundary conditions may simulate the effect of adenosine for hyperemia. Therefore, to perform the high-fidelity simulation, the computer system performing step 403 may solve the Navier-Stokes equations on the coronary arteries using the aforementioned boundary conditions.

Step 404 may include performing high-fidelity simulation of blood flow using boundary conditions obtained based on the modified patient model, to obtain a second high-fidelity solution. In general, the high-fidelity simulation of step 404 may be performed on extrema corresponding to configuration(s) in which the coronary arteries are fully revascularized. Such extrema serves as an example of the extrema of configurations to be explored described above in connection with step 304 of FIG. 3. The revascularization may be one in which the entire anatomy of the patient-specific geometry is revascularized. The high-fidelity simulation of step 404 may be performed using a computational model constructed as a high-fidelity model, which may include boundary conditions derived from the modified patient model described above. The computational model of step 403 and the computational model of step 404 may be based on the same mathematical relationships, but with different boundary conditions and/or other parameters applied.

Step 405 may include, for each of the base patient model and the modified patient model, performing an additional high-fidelity simulation of blood flow at a different flow rate, to obtain third and fourth high-fidelity solutions. For example, the high-fidelity simulation performed in step 402 may be performed for a first flow rate, and step 405 may include a high-fidelity simulation performed in the same or substantially same manner (e.g., using boundary conditions based on the base patient model), but with a flow rate that is higher (e.g., 10%, 15%, 25%, 50%, or 75% higher) than the aforementioned first flow rate. Similarly, the high-fidelity simulation performed in step 403 may be performed for a second flow rate (which may be the same as the first flow rate), and step 405 may include a high-fidelity simulation that is performed in the same or substantially same manner (e.g., using boundary conditions based on the modified patient model) but with a flow rate that is higher (e.g., 10%, 15%, 25%, 50%, or 75% higher) than the aforementioned second flow rate. By performing additional simulations at different flow rate, the high-fidelity solutions obtained across steps 403-405 may be used to inform a reduced order model in which fluid resistance parameters depend on flow rate. With one additional simulation in each of the configurations associated respectively with the base patient model and the modified patient model, the fluid resistances in the reduced order model may depend linearly on flowrate.

Step 406 may include generating response surfaces respectively for the intercept and slope of the fluid resistance function. The response surfaces may be generated based on the four high-fidelity solutions obtained across steps 403-405, and may include two response surfaces, a first response surface for the intercept of the fluid resistance function, and a second response surface for the slope of the fluid resistance function. The first and second response surfaces may both be based on the one-dimensional Navier-Stokes equations. The first response surface may have the functional form $1/r^4$ for the intercept. The second response surface may have the functional form $(dA/dz*1/r^6)$ for the slope. In these expressions, r is the local radius, A is the area and dA/dz is the gradient of area along the vessel. It is noted that step 406 is an example of step 306 described above. Therefore, any techniques described in connection with step 306 are applicable to step 406.

Step 407 may include receiving a modified geometry. The modified geometry may be a geometry that is to be subject to reduced order simulation, and may be a revascularized geometry including of for example, locations at which the coronary arteries are to be revascularized and final size(s) of vessel lumen(s). The revascularized geometry may be a simulation input that is defined by user input, or by a simulation process. One or more configurations for reduced order modeling and simulation may be defined based on the revascularized geometry. For example, a value of an attribute of the vascularized geometry, such as a value of a location of revascularization and/or a value of the final size of a vessel lumen, may serve as a configuration or part of the configuration. Such configurations may be used on the response surface(s) to obtain parameter of the reduced order model(s) that is used in step 408 described below.

Step 408 may include performing reduced order simulation based on the revascularized geometry and the two response surfaces. The reduced-order simulation may be informed by interpolated values estimated using the response surfaces on the revascularized geometry. The reduced order simulation may be performed in real-time, and may use one or more reduced order models constructed as described above. Such reduced order model may have mathematical relationships in the form of expressions (3) and (4), and may be constructed such to yield the same results as the high fidelity model of process 510 for the four high-fidelity. It is noted that step 408 is an example of step 307 described above. Therefore, techniques described in connection with step 307 are generally applicable to step 408.

The output of the low fidelity simulation may be used to output the updated flowrates, blood pressures, FFR or any other quantity of interest, such as wall shear stress, for the configuration in step 403.

In the illustration of FIG. 5, process 510 serves as an example of the high-fidelity simulations of steps 403 to 405. As shown in FIG. 5, four Navier-Stokes simulations may be performed. These simulations may include a first Navier-Stokes simulation using hyperemic boundary conditions applied based on idealized model 504, a second Navier-Stokes simulation using superemic boundary conditions applied based on idealized model 504, a third Navier-Stokes simulation using superemic boundary conditions applied based on the base patient model 503, and a fourth Navier-Stokes simulation using hyperemic boundary conditions applied based on base patient model 503. It is noted that the aforementioned boundary conditions serve as examples of simulation parameters, and that the respective simulation parameters of four simulations may differ from one another in aspects other than the aforementioned boundary conditions.

The four sets of simulation parameters applied to the Navier-Stokes simulation may respectively result in four high-fidelity solutions, as described above in connection with step 406 of FIG. 4. The four high-fidelity solutions may then be used to build response surfaces (step 520), the process of which may include deriving parameters of the reduced order model. Item 504 in FIG. 4 is a visual depiction of a parameters of a reduced order model. The reduced order model may be a reduced order model having mathematical relationships in the form of expressions (3) and (4), and may be constructed such that the reduced order model yields the same results as the high fidelity model of process 510 for the four high-fidelity simulations.

FIG. 6 illustrates the probing of the responses surfaces for reduced order modeling. As shown, the response surface(s) may be probed based on configurations indicated by a modified geometry 601. Modified geometry 601 may be a revascularized geometry as described above for step 407, and may be representable in a graphical form, such as a three-dimensional graphical model (e.g., a surface mesh), as shown in FIG. 6. Modified geometry 601 may be an anatomical model, and may represent a particular anatomical geometry to be explored or analyzed by simulation; this geometry may, for example, be a state of the patient that is either natural or planned. Modified geometry 601 may differ from the idealized 505.

The probing of the response surface(s) may obtain values for the parameters of the reduced order model. The reduced order model may be executed to obtain a hemodynamic solution. In process 610, the hemodynamic solution may be graphically displayed along with the three-dimensional graphical model of the modified geometry 601. For example, the hemodynamic solution may be represented as in graphical form, and the graphics of the hemodynamic solution may be overlaid or otherwise combined with the three-dimensional graphical model of the modified geometry 610, to obtain a mapped model 602. The mapped model 602 may be, for example, displayed on an electronic display. Such display may be performed in real-time.

The methods described in this disclosure may have various clinical applications, include: planning a percutaneous coronary intervention (PCI) procedure; planning bypass graft surgery; modeling disease progression and regression of lesions; modeling positive and negative remodeling of lesions; sensitivity analysis, uncertainty quantification and/or estimation of confidence intervals for flow simulations; modeling of different physiologic conditions, such as exercise; modeling the effect of drugs, altitude or autoregulatory mechanisms.

In some embodiments, the methods described in this disclosure may be used to produce real-time updates of fractional flow reserve (FFR) (e.g., fractional flow reserve derived from computed tomography (FFRCT)) in response to a change in the vessel lumen geometry of a patient. This change in vessel lumen geometry may be a natural change, or a change that is expected to occur as a result of a candidate treatment for a patient. For example, the lumen geometry may be represented as one or more parameters, and a user or simulation process may adjust the values of such parameters to reflect the change in vessel lumen geometry. In response to adjustment of the modeling parameters, the computer system performing the simulation may identify configurations for reduced order modeling, probe response surface(s) based on the configurations to parameterize a reduced order model, and solve the reduced order model to compute value(s) of FFRCT. The response surface(s) may have been generated prior to the simulation, in accordance with the methods described in this disclosure (e.g., FIGS. 3 and 4). The computed value(s) of FFRCT may be output in any suitable manner (e.g., displayed on a display device, or transmitted to another computer system for display on a display device). The vessel lumen geometry may be part of the coronary arteries of the patient, or part of another vasculature portion.

Any method discussed in this disclosure that is understood to be computer-implementable, including the methods shown in FIGS. 2-6 and any computation described in connection with expressions (1) to (11), may be performed by one or more processors of a computer system. A step of a method performed by one or more processors may also be referred to as an operation.

FIG. 7 depicts an example of an environment in which such a computer system may be implemented as server systems 740. In addition to server systems 740, the environment of FIG. 7 further includes a plurality of physicians 720 and third party providers 730, any of which may be connected to an electronic network 710, such as the Internet, through one or more computers, servers, and/or handheld mobile devices. In FIG. 1, physicians 720 and third party providers 730 may each represent a computer system, as well as an organization that uses such a system. For example, a physician 720 may be a hospital or a computer system of a hospital.

Physicians 720 and/or third party providers 730 may create or otherwise obtain medical images, such as images of the cardiac, vascular, and/or organ systems, of one or more patients. Physicians 720 and/or third party providers 730 may also obtain any combination of patient-specific information, such as age, medical history, blood pressure, blood viscosity, the anatomical information described above in connection with step 301 of the method of FIG. 3, and other types of patient-specific information. Physicians 720 and/or third party providers 730 may transmit the patient-specific information to server systems 740 over the electronic network 710.

Server systems 740 may include one or more storage devices 760 for storing images and data received from physicians 720 and/or third party providers 730. The storage devices 760 may be considered to be components of the memory of the server systems 740. Server systems 740 may also include one or more processing devices 750 for processing images and data stored in the storage devices and for performing any computer-implementable process described in this disclosure. Each of the processing devices 750 may be a processor or a device that include at least one processor.

In some embodiments, server systems 740 may have a cloud computing platform with scalable resources for computations and/or data storage, and may run an application for performing methods described in this disclosure on the cloud computing platform. In such embodiments, any outputs may be transmitted to another computer system, such as a personal computer, for display and/or storage.

Other examples of computer systems for performing methods of this disclosure include desktop computers, laptop computers, and mobile computing devices such as tablets and smartphones.

The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or another type of processing unit.

A computer system, such as server systems 740, may include one or more computing devices. If the one or more processors of the computer system is implemented as a plurality of processors, the plurality of processors may be included in a single computing device or distribute among a plurality of computing devices. If a computer system comprises a plurality of computing devices, the memory of the computer system may include the respective memory of each computing device of the plurality of computing devices.

In general, a computing device may include processor(s) (e.g., CPU, GPU, or other processing unit), a memory, and communication interface(s) (e.g., a network interface) to communicate with other devices. Memory may include volatile memory, such as RAM, and/or non-volatile memory, such as ROM and storage media. Examples of storage media include solid-state storage media (e.g., solid state drives and/or removable flash memory), optical storage media (e.g., optical discs), and/or magnetic storage media (e.g., hard disk drives). The aforementioned instructions (e.g., software or computer-readable code) may be stored in any volatile and/or non-volatile memory component of memory. The computing device may, in some embodiments, further include input device(s) (e.g., a keyboard, mouse, or touchscreen) and output device(s) (e.g., a display, printer). The aforementioned elements of the computing device may be connected to one another through a bus, which represents one or more busses. In some embodiments, the processor(s) of the computing device includes both a CPU and a GPU.

Instructions executable by one or more processors may be stored on a non-transitory computer-readable medium. Therefore, whenever a computer-implemented method is described in this disclosure, this disclosure shall also be understood as describing a non-transitory computer-readable medium storing instructions that, when executed by one or more processors, configure or cause the one or more processors to perform the computer-implemented method. Examples of non-transitory computer-readable medium include RAM, ROM, solid-state storage media (e.g., solid state drives), optical storage media (e.g., optical discs), and magnetic storage media (e.g., hard disk drives). A non-transitory computer-readable medium may be part of the memory of a computer system or separate from any computer system. An "electronic storage device" may include any of the non-transitory computer-readable media described above.

It should be appreciated that in the above description of exemplary embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the disclosure, and it is intended to claim all such changes and modifications as falling within the scope of the disclosure. For example, functionality may be added or deleted from the block diagrams and operations may be interchanged among functional blocks. Steps may be added or deleted to methods described within the scope of the present disclosure.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted.

What is claimed is:

1. A computer-implemented method for blood flow simulation, the method comprising:
   performing a plurality of blood flow simulations using a first model of vascular blood flow, each of the plurality of blood flow simulations simulating blood flow in a vasculature of a patient or a geometry based on the vasculature of the patient;
   based on results of the plurality of blood flow simulations, generating a response surface, the response surface comprising a polynomial mapping one or more first parameters of the first model to one or more second parameters of a reduced order model of vascular blood flow having lower fidelity than that of the first model;
   determining values for the one or more parameters of the reduced order model mapped, by the response surface, from parameter values representing a modified state of the vasculature; and
   performing simulation of blood flow in the modified state of the vasculature using the reduced order model parameterized by the determined values for the one or more second parameters, to determine a blood flow characteristic of the modified state of the vasculature,
   wherein the plurality of blood simulations are performed for a plurality of configurations, respectively, each configuration representing a different vascular geometry derived from a geometry of the vasculature of the patient and/or a physiological state,
   the results of the plurality of blood flow simulations are first simulation results respectively obtained for the plurality of configurations,
   each of the plurality of configuration include first values for the one or more first parameters, and
   the generating the response surface includes:
   for each of the plurality of configurations, determining second values for the one or more second parameters that, when used in low-fidelity blood flow simulation performed using the reduced order model, produce a respective second simulation result that matches the respective first simulation result; and
   generating the response surface based on the first values for the one or more first parameters and the determined second values for the one or more second parameters for each of the plurality of configurations.

2. The method of claim 1, wherein
   each of the plurality of configurations including values, for the first parameters, that represent at least a respective vascular geometry in which blood flow is simulated in the respective blood flow simulation, and
   the plurality of configurations include:
   a first configuration representing the vasculature of the patient; and
   one or more further configurations, each representing a vascular geometry derived from a geometry the vasculature and/or a physiological state different from a physiological state represented by the first configuration.

3. The method of claim 2, further comprising:
   receiving patient-specific image data of the vasculature of the patient;
   generating a patient-specific anatomical model of the vasculature based the image; and
   based on the patient-specific anatomical model, determining values of the one or more first parameters for the first configuration to represent a patient-specific geometry of the vasculature.

4. The method of claim 2, wherein the one or more further configurations include one or more extrema configurations each representing a state of the vasculature at an anatomical limit or a physiological limit.

5. The method of claim 4, wherein
   the vasculature is at least a portion of coronary arteries of the patient, and
   at least one of the one or more extrema configurations represents a full revascularization of the at least the portion of coronary arteries.

6. The method of claim 4, wherein the one or more further configurations further include one or more configurations determined using a sampling or quadrature method based on the one or more extrema configurations.

7. The method of claim 6, wherein
   the response surface is a surface fitted to a set of points, and
   each point in the set of points includes determined values for the one or more second parameters determined for a respective one of the plurality of configurations.

8. The method of claim 1, wherein the vasculature includes at least one of coronary vasculature, peripheral vasculature, cerebral vasculature, renal vasculature, visceral vasculature, or hepatic vasculature.

9. The method of claim 1, wherein
   each of the plurality of blood flow simulation are performed in real time, such that values of the blood flow characteristic are determined in real time, and
   values of the blood flow characteristic are presented to a user in real time.

10. The method of claim 1, wherein the blood flow characteristic is fractional flow reserve.

11. A computer system for blood flow simulation, comprising:
    a memory storing instructions;
    one or more processors configured to execute the instructions to perform a method including:
    performing a plurality of blood flow simulations using a first model of vascular blood flow, each of the plurality of blood flow simulations simulating blood flow in a vasculature of a patient or a geometry based on the vasculature of the patient;
    based on results of the plurality of blood flow simulations, generating a response surface, the response surface comprising a polynomial mapping one or more first parameters of the first model to one or more second parameters of a reduced order model of vascular blood flow having lower fidelity than that of the first model;

determining values for the one or more parameters of the reduced order model mapped, by the response surface, from parameter values representing a modified state of the vasculature; and performing simulation of blood flow in the modified state of the vasculature using the reduced order model parameterized by the determined values for the one or more second parameters, to determine a blood flow characteristic of the modified state of the vasculature, wherein the plurality of blood simulations are performed for a plurality of configurations, respectively, each configuration representing a different vascular geometry derived from a geometry of the vasculature of the patient and/or a physiological state, the results of the plurality of blood flow simulations are first simulation results respectively obtained for the plurality of configurations, each of the plurality of configuration include first values for the one or more first parameters, and the generating the response surface includes:

for each of the plurality of configurations, determining second values for the one or more second parameters that, when used in low-fidelity blood flow simulation performed using the reduced order model, produce a respective second simulation result that matches the respective first simulation result; and generating the response surface based on the first values for the one or more first parameters and the determined second values for the one or more second parameters for each of the plurality of configurations.

12. The computer system of claim 11, wherein each of the plurality of configurations including values, for the first parameters, that represent at least a respective vascular geometry in which blood flow is simulated in the respective blood flow simulation, and the plurality of configurations include:

a first configuration representing the vasculature of the patient; and one or more further configurations, each representing a vascular geometry derived from a geometry the vasculature and/or a physiological state different from a physiological state represented by the first configuration.

13. The computer system of claim 12, further comprising:

receiving patient-specific image data of the vasculature of the patient;

generating a patient-specific anatomical model of the vasculature based the image; and based on the patient-specific anatomical model, determining values of the one or more first parameters for the first configuration to represent a patient-specific geometry of the vasculature.

14. The computer system of claim 12, wherein the one or more further configurations include one or more extrema configurations each representing a state of the vasculature at an anatomical limit or a physiological limit.

15. The computer system of claim 14, wherein the vasculature is at least a portion of coronary arteries of the patient, and at least one of the one or more extrema configurations represents a full revascularization of the at least the portion of coronary arteries.

16. The computer system of claim 14, wherein the one or more further configurations further include one or more configurations determined using a sampling or quadrature method based on the one or more extrema configurations.

17. The computer system of claim 11, wherein the response surface is a surface fitted to a set of points, and each point in the set of points includes determined values for the one or more second parameters determined for a respective one of the plurality of configurations.

18. A non-transitory computer-readable medium storing instructions that, when executed by one or more processors, cause the one or more processors to perform a method comprising:

performing a plurality of blood flow simulations using a first model of vascular blood flow, each of the plurality of blood flow simulations simulating blood flow in a vasculature of a patient or a geometry based on the vasculature of the patient;

based on results of the plurality of blood flow simulations, generating a response surface, the response surface comprising a polynomial mapping one or more first parameters of the first model to one or more second parameters of a reduced order model of vascular blood flow having lower fidelity than that of the first model;

determining values for the one or more parameters of the reduced order model mapped, by the response surface, from parameter values representing a modified state of the vasculature; and performing simulation of blood flow in the modified state of the vasculature using the reduced order model parameterized by the determined values for the one or more second parameters, to determine a blood flow characteristic of the modified state of the vasculature, wherein the plurality of blood simulations are performed for a plurality of configurations, respectively, each configuration representing a different vascular geometry derived from a geometry of the vasculature of the patient and/or a physiological state, the results of the plurality of blood flow simulations are first simulation results respectively obtained for the plurality of configurations, each of the plurality of configuration include first values for the one or more first parameters, and the generating the response surface includes:

for each of the plurality of configurations, determining second values for the one or more second parameters that, when used in low-fidelity blood flow simulation performed using the reduced order model, produce a respective second simulation result that matches the respective first simulation result; and generating the response surface based on the first values for the one or more first parameters and the determined second values for the one or more second parameters for each of the plurality of configurations.

* * * * *

UNITED STATES PATENT AND TRADEMARK OFFICE
CERTIFICATE OF CORRECTION

PATENT NO. : 11,707,325 B2
APPLICATION NO. : 16/875767
DATED : July 25, 2023
INVENTOR(S) : Sethuraman Sankaran et al.

Page 1 of 1

It is certified that error appears in the above-identified patent and that said Letters Patent is hereby corrected as shown below:

On the Title Page

Item (54) and in the Specification, Column 1 Lines 1-4, In the Title, delete "SYSTEM" and insert --SYSTEMS--.

In the Claims

In Column 22 Line 10, In Claim 2, after "geometry" insert --of--.

In Column 22 Line 18, In Claim 3, after "based" insert --on--.

In Column 23 Line 45, In Claim 12, after "geometry" insert --of--.

In Column 23 Line 53, In Claim 13, after "based" insert --on--.

Signed and Sealed this
Sixth Day of May, 2025

Coke Morgan Stewart
*Acting Director of the United States Patent and Trademark Office*